United States Patent [19]

Meinershagen

[11] Patent Number: 4,854,867
[45] Date of Patent: Aug. 8, 1989

[54] DENTAL TOOL FOR FACILITATING GINGIVAL RETRACTION

[75] Inventor: Charles I. Meinershagen, Redding, Calif.

[73] Assignee: NewTech Products, Inc., Palo Cedro, Calif.

[21] Appl. No.: 149,311

[22] Filed: Jan. 28, 1988

[51] Int. Cl.⁴ .............................................. A61C 9/00
[52] U.S. Cl. ................................. 433/40; 433/142; 433/143
[58] Field of Search ............... 433/141, 143, 142, 144, 433/156, 40, 50, 80, 83, 89

[56] References Cited

U.S. PATENT DOCUMENTS

| | | | |
|---|---|---|---|
| 881,722 | 3/1908 | Szusser | 433/144 |
| 1,691,786 | 11/1928 | Roth | 433/143 |
| 2,552,134 | 5/1957 | Berliner | 433/143 |
| 4,270,902 | 2/1981 | Wiland | 433/143 |

Primary Examiner—Robert Peshock
Attorney, Agent, or Firm—Townsend & Townsend

[57] ABSTRACT

A dental tool for facilitating gingival retraction.

A shank coupled to a handle terminates in a working end member having a curved edge shaped to generally conform to the curvature of the root surface of a tooth at the gingival level and also to the contour of the marginal gingiva. The exact shape of the curved edge varies with the type of tooth for which the tool is designed.

The tool can also be used for shielding the gingiva from a cutting tool working close to the gingiva, and as an aid in installing a rubber dental dam.

6 Claims, 1 Drawing Sheet

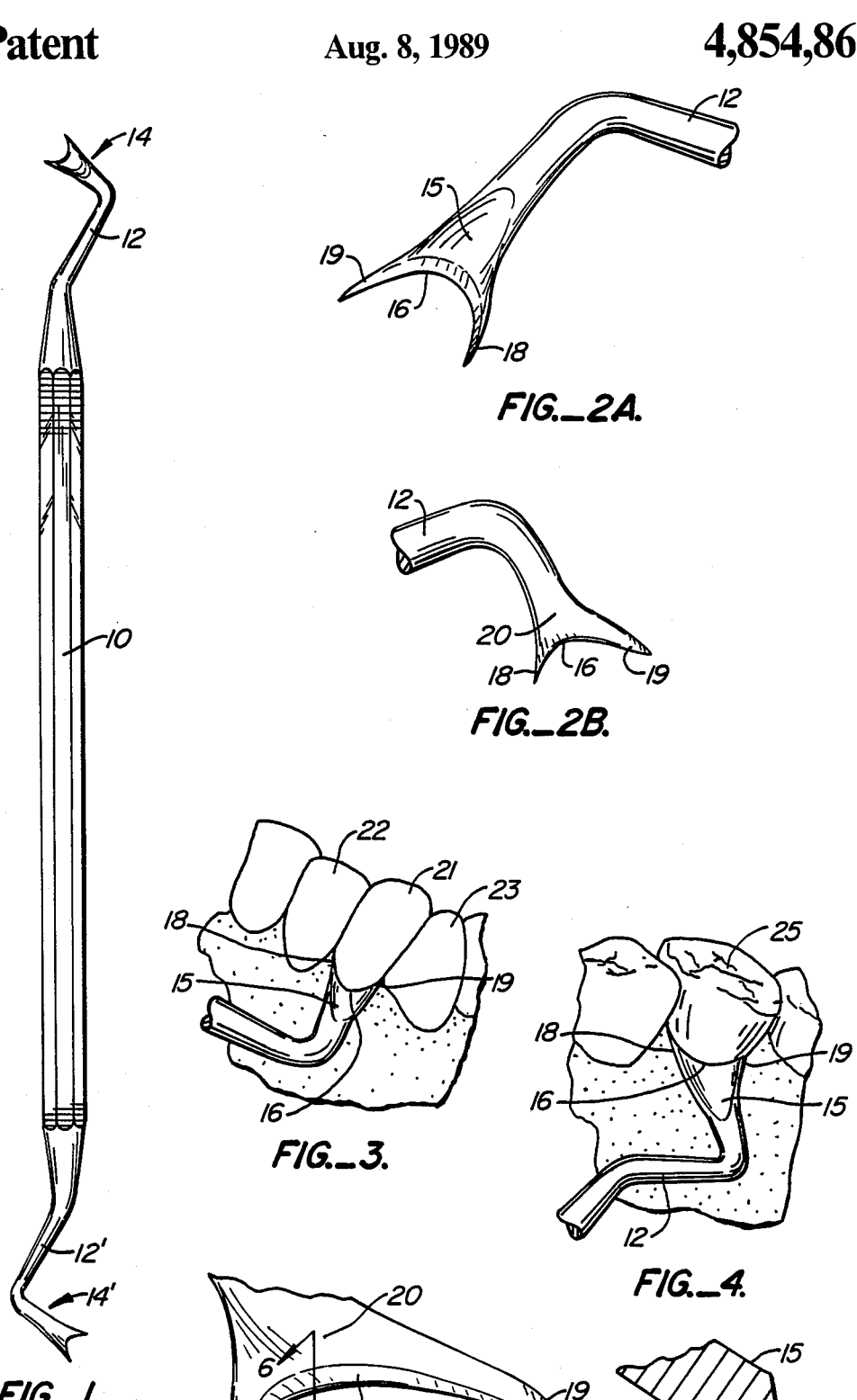

DENTAL TOOL FOR FACILITATING GINGIVAL RETRACTION

BACKGROUND OF THE INVENTION

This invention relates to dental instruments used to facilitate cavity repairs.

In dentistry it is a common practice to repair cavities by drilling out the decayed material to form a cavity preparation, and filling the cavity preparation with some type of restoration material. A very common cavity found on the tooth surface is the facial or lingual cavity in the gingival or subgingival area of the crown of the tooth. This type of cavity is common due to the shape of the marginal gingiva next to the tooth surface, which has a natural tendency to collect food and plaque.

In order to place either an amalgam or composite restoration material in this area, the gingiva must be retracted from the cavity region for a sufficiently long time period to keep the cavity preparation dry and free from blood and saliva so as not to contaminate the filling material while it is being emplaced. In today's practice this required retraction is usually accomplished by the use of a flat bladed spatula type instrument. Due to the shape of the spatula type instrument, the marginal gingiva is usually irritated, lacerated or torn during retraction, which does not guarantee that the cavity preparation will be kept dry and free from fluid contamination and which also leads to deterioration of the gingival tissue, both of which are undesirable.

Another instrument used in present practice to retract the gingiva is the rubber dam clamp, which is time consuming to install, awkward to use, and typically retracts only that portion of the gingiva positioned centrally of the root surface of the tooth at the gingival level.

SUMMARY OF THE INVENTION

The invention comprises a dental tool which facilitates gingival retraction and which substantially reduces or entirely eliminates irritation, laceration and tearing of the marginal gingiva.

In its broadest aspect, the invention comprises a dental tool having a shank terminating in a working end member, the working end member having a curved edge shaped to generally conform to the curvature of the root surface of tooth at the gingival level and to the contour of the marginal gingiva. The working end member includes a concave face terminating in the curved edge.

In a more specific aspect, the invention comprises a dental tool including a handle portion with first and second ends, a first shank coupled to the first end and terminating in a first working end member extending at a first angle with respect to the handle portion and having a curved edge, a second shank coupled to the second end of the handle portion and terminating in a second working end member extending at a second angle with respect to the handle portion and also having a curved edge. Both curved edges are shaped to generally conform to the curvature of the root surface of a tooth at the gingival level and to the contour of the marginal gingiva. Each working end member also includes a concave face terminating in its associated curved edge, each concave face being located on the opposite side of a plane passing through the longitudinal axis of the handle portion. The first and second angles are arranged so that the first and second working end members extend in generally opposite directions from the handle portion to provide right and left handed working end members for the tool. Preferably, the first shank, the second shank and the handle portion are of unitary construction.

In a more specific aspect of the invention, the tools are constructed with working end members of different sizes, with three different sizes being typical. A first size has a relatively long face and narrow width with a relatively small radius of curvature in order to conform to the root surface curvature and marginal gingiva contour of the mandibular anterior incisors. A second size has a relatively short and wide shape in order to fit the posterior molars and wide bicuspids. Still a third size is a medium or middle size adapted to fit the average bicuspid, canine and maxillary incisor.

For a fuller understanding for the nature and advantages of the invention, reference should be had to the ensuing detailed description taken in conjunction with the accompanying drawings.

BRIEF DESCRIPTION OF THE DRAWINGS

FIG. 1 is a plan elevational view of a tool incorporating the invention;

FIG. 2A is an enlarged perspective view showing a working end of the tool;

FIG. 2B is an enlarged perspective view showing the reverse side of the working end of the tool from that depicted in FIG. 2A;

FIG. 3 illustrates a first specific embodiment of the invention designed for use with a smaller tooth:

FIG. 4 illustrates another specific embodiment of the invention for use with a large tooth;

FIG. 5 is an enlarged view similar to FIG. 2B of an alternate embodiment of the invention; and FIG. 6 is a sectional view taken along lines 6—6 of FIG. 5.

DESCRIPTION OF THE PREFERRED EMBODIMENTS

Turning now to the drawings. FIG. 1 illustrates a compound dental tool incorporating the invention. As seen in this FIG., the tool includes a central handle portion 10 and a pair of working ends. A first working end includes a shank portion 12 terminating in a working end member generally designated with reference numeral 14. Working end member 14 has a concave face 15 which terminates in a curved edge 16 having corner portions 18, 19. As can be seen from FIG. 2B, the face 20 of the working end member 14 opposite from the concave face 15 is generally convex. In the tool shown in FIG. 1, the opposite end from end 14 is essentially identical in configuration: Consequently, the same numerals have been employed to designate the shank and the working end member, with prime symbols used to distinguish the two.

The contour of the edge 16 and the extent of the corner portions 18, 19 are selected with two criteria in mind. Firstly, edge 16 must be shaped to generally conform to the curvature of the root surface of a tooth at the gingival level. This shape is necessary in order to facilitate retraction of the gingiva. The second criterion is to provide sufficient extent to the corner portions 18, 19 so that the marginal gingiva around the corners of the tooth can also be retracted during use of the tool.

FIG. 3 illustrates the use of working end member 14 for a small tooth, such as a mandibular anterior incisor 21. As seen in this FIG., edge 16 closely fits the curvature of the root surface of the tooth 21, while corner edges 18, 19 extend into the interproximal regions between the tooth 21 and the adjacent teeth 22, 23. In use, the working end 14 is installed with the convex face 20 facing the gingiva, and the tool is then manipulated by means of the handle 10 so that the convex face 20 presses against the gingiva across the contour of the root surface and around the corners of the tooth 21. Slight downward pressure against the gingiva causes the tissue to blanch, which momentarily halts any bleeding or seepage. However, due to the contour of edge 16 and the extent of the corner portions 18, 19, the gingiva is not lacerated.

The double ended configuration illustrated in FIG. 1 has essentially identical working end members designed for use with the mandibular anterior incisors, which tend to be long and narrow. As can be seen in FIG. 1, the upper working end member 14 is arranged such that the concave surface faces out of the page, while the lower end is arranged with the concave surface facing into the page. Also, the angle of extension of upper working end member 14 with respect to the longitudinal axis of handle portion 10 is essentially opposite that of the angle of extension of the lower working end member. As a consequence, the compound tool depicted in FIG. 1 can be used as both a right handed and left handed instrument, thereby enabling the operator to reach all of the quadrants of the dentition with either the right or the left hand.

As noted above, the working end member 14 depicted in FIGS. 1-3 is specifically designed for use with mandibular anterior incisors. FIG. 4 illustrates another embodiment of the invention designed for use with the posterior molars and wide bicuspids such as molar 25 illustrated in the FIG. As is evident from FIG. 4, the contour of edge 16 is much shallower than that of the embodiment of FIGS. 1-3 in order to accommodate the different curvature of the root surface of the molar 25. The corner portions 18, 19 are correspondingly less pronounced, and the concave face 15 is substantially broader than that of the incisor embodiment. The hidden face of the FIG. 4 embodiment is convex, in a manner similar to that of the embodiment of FIGS. 1-3. These dimensional differences are due to the different structure of the molar tooth 25. The use and function of the FIG. 4 embodiment is the same as that described above: viz., to enable retraction of the gingiva without irritation, laceration or tearing.

As will be appreciated by those skilled in the art, the embodiments illustrated in FIGS. 1-4 represent the two relative extremes in the spectrum of tooth shape and marginal gingiva configuration. Lying intermediate the mandibular anterior incisors and the class including the posterior molars and wide bicuspids are the teeth classified as the average bicuspids, canines and maxillary incisors. For teeth in this category, a tool having a shape generally intermediate the two extremes illustrated in FIGS. 1-4 is provided. For conciseness, a tool of this intermediate shape has not been illustrated.

All embodiments of the tool can be fabricated from metal, such as stainless steel and titanium, plastic and nylon. Other suitable materials will occur to those skilled in the art.

Although lower face 20 is depicted in FIG. 2B as generally convex, if desired this face may have a more complex shape to provide a more accurate match to the shape of the marginal gingiva. For example, FIGS. 5 and 6 illustrate an alternate embodiment of the invention in which the portion of the lower face 20 adjacent the edge 16 has a slight concave contour 29 to match the contour of the marginal gingiva.

In addition to the principal use noted above, the tool may also be used for other purposes. For example, when installing a rubber dental dam, the tool can be used to tuck in the portions of the dam between the teeth. In addition, the tool can be used as an effective shield between the gingiva and/or a rubber dam and a cutting tool working close to the gingiva, even though the cavity may lie above the gingiva. In both shield and retraction applications, the concave face 15 affords maximum exposure to the operator of the tooth surface under repair.

While the above provides a full and complete disclosure of the invention, various modifications, alternate constructions and equivalents will occur to those skilled in the art. For example, while the compound tool of FIG. 1 has been illustrated with opposite working end members of substantially identical configuration, the end members may be mixed, if desired, to provide curved edges designed to accommodate two different types of teeth. In addition, it is understood that the shape of the curved edge 16 is not precise, but an approximation of the general curvature of the root surface of a particular type of tooth and the contour of the marginal gingiva. Further, while the shank, working end member and handle portion have been illustrated and described as unitary, these individual elements may be discrete and fastened together in any suitable manner. Therefore, the above should not be construed as limiting the invention, which is defined by the appended claims.

What is claimed is:

1. A dental tool for facilitating gingival retraction comprising a shank terminating in a working end member, said working end member having a concave face extending along the body axis of said member and terminating in a curved edge shaped to generally conform to the curvature of the root surface of a tooth at the gingival level and to the contour of the marginal gingival, said concave face being laterally concave with respect to said body axis.

2. The invention of claim 1 further including a handle portion coupled to said shank.

3. The invention of claim 2 wherein said shank and said handle portion are unitary.

4. A dental tool for facilitating gingival retraction comprising:
   a handle portion having first and second ends;
   a first shank coupled to said first end and terminating in a first working end member extending at a first angle with respect to said handle portion, said first working end member having a concave face extending along the body axis of said member and terminating in a first curved edge; and
   a second shank coupled to said second end and terminating in a second working end member extending at a second angle with respect to said handle portion, said second working end member having a concave face extending along the body axis thereof and terminating in a second curved edge;
   said first and second curved edges being shaped to generally conform to the curvature of the root surface of a tooth at the gingival level and to the contour of the marginal gingiva, each of said concave faces being laterally concave with respect to the body axis of the associated working end member;

said first and second angles being arranged so that said first and second working end members extend at generally opposite directions from said handle portion.

5. The invention of claim 4 wherein said concave faces are oppositely disposed with respect to a plane passing through the longitudinal axis of said handle portion.

6. The invention of claim 5 wherein said said first shank, said second shank and said handle portion are unitary.

* * * * *